United States Patent
Fodor

(10) Patent No.: US 7,199,271 B2
(45) Date of Patent: Apr. 3, 2007

(54) METHOD FOR REDUCING CYCLOHEXENONE CONTENT OF A CYCLOHEXENONE-CONTAINING ORGANIC MIXTURE

(75) Inventor: Ludovic Fodor, Beaumont, TX (US)

(73) Assignee: Invista North America S.A.R.L., Wilmington, DE (US)

( * ) Notice: Subject to any disclaimer, the term of this patent is extended or adjusted under 35 U.S.C. 154(b) by 0 days.

(21) Appl. No.: 10/925,103

(22) Filed: Mar. 17, 2005

(65) Prior Publication Data
US 2006/0211890 A1  Sep. 21, 2006

(51) Int. Cl.
*C07C 45/78* (2006.01)
(52) U.S. Cl. .................. 568/366; 568/377
(58) Field of Classification Search .............. None
See application file for complete search history.

(56) References Cited

U.S. PATENT DOCUMENTS

| 2,813,905 | A |   | 11/1957 | Lyons et al. |          |
|-----------|---|---|---------|--------------|----------|
| 4,929,762 | A | * | 5/1990  | Matsunaga et al. | 568/361 |
| 5,292,762 | A |   | 3/1994  | Hsu          |          |
| 5,292,960 | A | * | 3/1994  | Meier et al. | 568/366  |
| 6,075,169 | A |   | 6/2000  | Rehfinger et al. |      |

FOREIGN PATENT DOCUMENTS

| DE | 1123184   |   | 5/1971 |
|----|-----------|---|--------|
| DE | 2650892   |   | 6/1978 |
| EP | 0260076   |   | 3/1988 |
| EP | 0788292   | A | 4/1997 |
| EP | 1433774   | A | 6/2004 |
| EP | 0659726   | A | 6/2006 |
| JP | 08-019019 |   | 2/1998 |

\* cited by examiner

*Primary Examiner*—Sikarl A. Witherspoon

(57) ABSTRACT

A method for reducing the concentration of cyclohexenone in a cyclohexenone containing organic mixture is disclosed. The method includes contacting an organic mixture comprising cyclohexenone with an effective amount of at least one of sulfurous acid, a salt of sulfurous acid, an alkali hydroxide, or a mixture of two or more of these compounds.

23 Claims, 2 Drawing Sheets

METHOD FOR REDUCING CYCLOHEXENONE CONTENT OF A CYCLOHEXENONE-CONTAINING ORGANIC MIXTURE

FIELD OF THE INVENTION

Exemplary embodiments of the present invention relate to a method of reducing cyclohexenone concentration in an organic mixture containing cyclohexenone.

BACKGROUND

Caprolactam has extensive commercial use, including its use in making nylon, such as nylon 6 for example, via condensation polymerization. Existing technology for producing caprolactam, particularly ε-caprolactam, on a commercial scale involves the reaction of cyclohexanone with a hydroxylamine salt to form a cyclohexanone oxime intermediate. Cyclohexanone oxime undergoes Beckmann rearrangement upon treatment with concentrated sulfuric acid to form ε-caprolactam.

Cyclohexanone is typically produced from cyclohexane that has been air oxidized to make a cyclohexanol-cyclohexanone mixture followed by dehydrogenation of the cyclohexanol in the mixture to produce more cyclohexanone. Several impurities are normally present in the cyclohexanol-cyclohexanone mixture obtained from air-oxidation of cyclohexane. Such impurities may include esters, carboxylic acids and cyclohexenone, particularly 2-cyclohexene-1-one. Several methods have been proposed for removing esters and carboxylic acids from cyclohexanol-cyclohexanone mixture.

DE 2,123,184 relates to a saponification method for decomposing the esters in alcohol, especially cyclohexanol, in the residues remaining after cyclohexanol-cyclohexanone distillation. In this way, additional cyclohexanol is obtained that results in a higher yield.

DE 2,650,892 relates to reducing caustic consumption during the treatment of acid and ester by-products by using an alkali hydroxide and carbonate and recycling some of the cyclohexane oxidation off-gas.

Japanese patent J08-019019 relates to eliminating esters and carboxylic acids from mixtures obtained during cyclohexane oxidation in presence of boron products with two step saponification.

Although methods have been taught to remove esters and carboxylic acids from organic mixtures, no method has previously been taught for removing cyclohexenone from organic mixtures of cyclohexenone and compounds such as cyclohexanone or a cyclohexanol-cyclohexanone mixture. If not removed from an organic mixture that is later used in caprolactam production, the cyclohexenone transforms to cyclohexenone oxime, typically 2-cyclohexene-1-one oxime, during the cyclohexanone oxime preparation of the caprolactam production process.

The formation of 2-cyclohexene-1-one oxime is detrimental because it consumes hydroxylamine, a raw material for caprolactam production and may also cause quality problems during polycondensation of the caprolactam during nylon production.

SUMMARY OF THE INVENTION

Therefore, it may be desirable to reduce cyclohexenone from certain organic mixtures, such as those used in caprolactam manufacture, by way of example only.

Embodiments of the invention are directed to a method for reducing the cyclohexenone content of a cyclohexenone-containing organic mixture. The method comprises treating the organic mixture with an effective amount of an additive comprising at least one of sulfurous acid, a salt of sulfurous acid, or an alkali hydroxide.

DETAILED DESCRIPTION OF EMBODIMENTS

Figure 1:
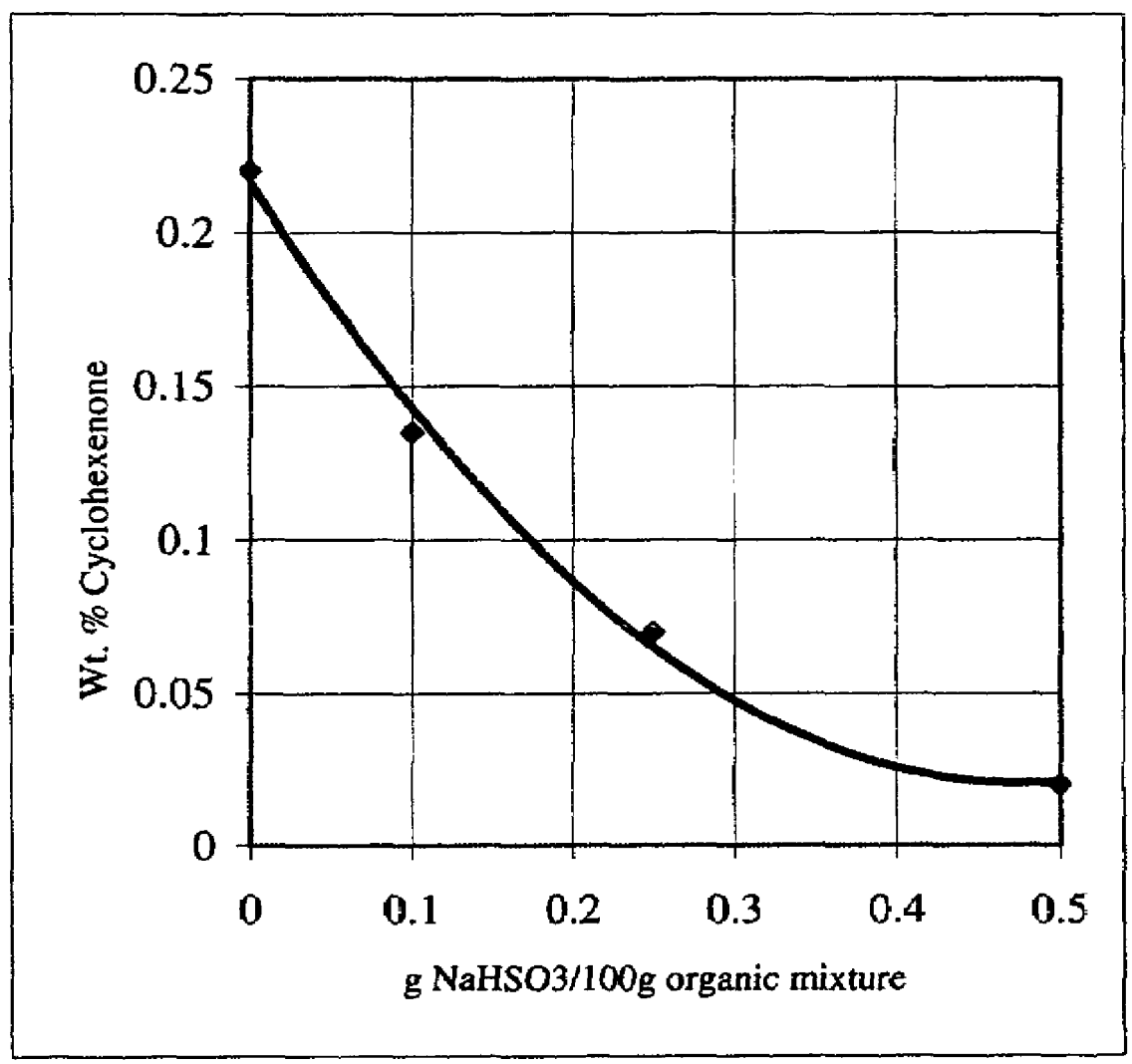
FIG. 1 is a graphical representation of the effect of a weak acid salt on cyclohexenone concentration added to an organic mixture containing cyclohexenone.

Embodiments of the invention are directed to a method for reducing the cyclohexenone content of a cyclohexenone-containing organic mixture. The method comprises treating the organic mixture with an effective amount of additive comprising at least one of sulfurous acid, a salt of sulfurous acid, or an alkali hydroxide. The additive may comprise a mixture of two or more of these compounds. The additive is added to the organic mixture in an amount effective to reduce the concentration of cyclohexenone in the organic mixture by about 75% of the original concentration of cyclohexenone prior to treatment.

As discussed herein, references are primarily made to a method for reducing content of cyclohexenone, such as 2-cyclohexene-1-one, in an organic mixture that also comprises cyclohexanone. It should be appreciated however, that the invention may be used to reduce cyclohexenone concentration in other organic mixtures as well.

As discussed above, cyclohexanone is typically produced by oxidizing cyclohexane in air to produce an organic mixture that typically includes a mixture of cyclohexanone and cyclohexanol as well as impurities including cyclohexenone, usually 2-cyclohexene-1-one. The physical properties of cyclohexenone are similar to those of cyclohexanol and cyclohexanone, making separation of cyclohexenone from cyclohexanol and/or cyclohexanone by distillation difficult. According to exemplary embodiments of the invention, the cyclohexenone concentration in the organic mixture is reduced by chemical treatment of the cyclohexenone in the mixture. The cyclohexenone concentration is reduced by at least about 75%, preferably by about 90% or greater, of the original concentration of cyclohexenone in the organic mixture.

In order to reduce cyclohexenone content of an organic mixture, such as an organic mixture comprising cyclohexanone and cyclohexenone for example, the organic mixture is treated with an effective amount of an additive or combination of additives including sulfurous acid, a salt of sulfurous acid, or an alkali hydroxide. A salt of sulfurous acid is meant to include a salt of pyrosulfurous acid, such as a metabisulfite. The treatment is typically conducted at a temperature in the range of about 60 to about 160 degrees C. and may last for about 10 to about 90 minutes, typically greater than 30 minutes. The organic mixture should be stirred during treatment to facilitate good mixing of the additive(s) with the cyclohexenone.

Reducing the concentration of the cyclohexenone in the organic mixture provides a mixture that may then be used in caprolactam production that decreases competition for hydroxylamine during the caprolactam production process, resulting in fewer side reactions consuming raw material.

Exemplary salts of sulfurous acid that may used include sodium metabisulfite, sodium hydrogen sulfite and sodium sulfite. Alkali hydroxides typically include sodium hydroxide, potassium hydroxide, or a mixture of the two. Preferably, sodium hydroxide is added to treat the organic mixture and reduce the concentration of cyclohexenone.

It should be appreciated that in cases where an alkali hydroxide is used as an additive for treatment, if the organic mixture containing cyclohexenone does not already contain cyclohexanone, the organic mixture should be spiked with cyclohexanone prior to treating it with the alkali hydroxide. When alkali hydroxides are used to treat the organic mixture, it is believed that the cyclohexenone concentration is decreased by reacting with cyclohexanone to form a dimer that, unlike cyclohexenone, is unreactive with hydroxylamine during caprolactam production.

The amount of cyclohexanone added may be enough to make the organic mixture about 1% to about 5% by weight cyclohexanone, although greater amounts of cyclohexanone may be added.

Where a sulfurous acid salt is used to reduce the concentration of cyclohexenone in the organic mixture, sodium hydrogen sulfite or sodium metabisulfite may be particularly effective when the organic mixture does not contain any cyclohexanone. Additionally, where sulfurous acid salts are used, more effective treatment may be achieved by adding sodium carbonate. The sodium carbonate is believed to stabilize the organic mixture and reduce reformation of cyclohexenone. For example, a mixture of sodium hydrogen sulfite and sodium carbonate or a mixture of sodium metabisulfite and sodium carbonate may advantageously be used in the treatment of the organic mixture.

The organic mixture may be a cyclohexenone-containing cyclohexanol-cyclohexanone mixture obtained from a process of cyclohexane oxidation. The oxidation may occur in any oxygenated environment, such as pure oxygen or air. In either case, distillation may be required to remove the oxidation products from unreacted cyclohexane. Following treatment according to methods consistent with exemplary embodiments of the present invention, the cyclohexenone depleted cyclohexanol-cyclohexanone mixture may then be dehydrogenated. This dehydrogenation converts the cyclohexanol to cyclohexanone, resulting in a feed particularly suitable for caprolactam production that is primarily cyclohexanone.

It should be appreciated that the treatment and/or any distillation may occur either before or after dehydrogenating the cyclohexanol. For example, the cyclohexenone containing organic mixture to be treated may already be predominantly cyclohexanone if treatment follows, rather than precedes, dehydrogenation of the cyclohexanol-cyclohexanone mixture.

Another example of an organic mixture from which it may be desirable to remove cyclohexenone includes cyclohexanol obtained from a process of making cyclohexanol from phenol, which typically results in an organic mixture of cyclohexanol with cyclohexenone impurities.

The cyclohexenone-depleted cyclohexanone produced by the method of the invention is suitable for caprolactam production.

EXAMPLES

The following non-limiting examples exemplify the method of the present invention.

Example 1

A 200 mL solution of KA oil containing 55.82 wt % cyclohexanone, 43.96 wt % cyclohexanol, and 0.22 wt % 2-cyclohexene-1-one was added to a 500 mL glass reactor provided with a heating mantle, stirring bar, temperature control, reflux condenser, and containing sample addition/withdrawing ports. The mixture was treated with 0.1 g of sodium hydrogen sulfite for 30 minutes at about 95 degrees C. under constant stirring.

The experiment was repeated, varying only the amount of sodium hydrogen sulfite added. The repeated experiments were conducted at levels of 0.25 g and 0.5 g of sodium hydrogen sulfite. A plot of cyclohexenone concentration in the organic mixture after the treatment as a function of the sodium hydrogen sulfite added is shown in FIG. 1. As FIG. 1 demonstrates, treating the organic mixture with sodium hydrogen sulfite for 30 minutes at 95 degrees C. may cause a reduction of up to about 90% of the initial cyclohexenone content.

Example 2

Figure 2:
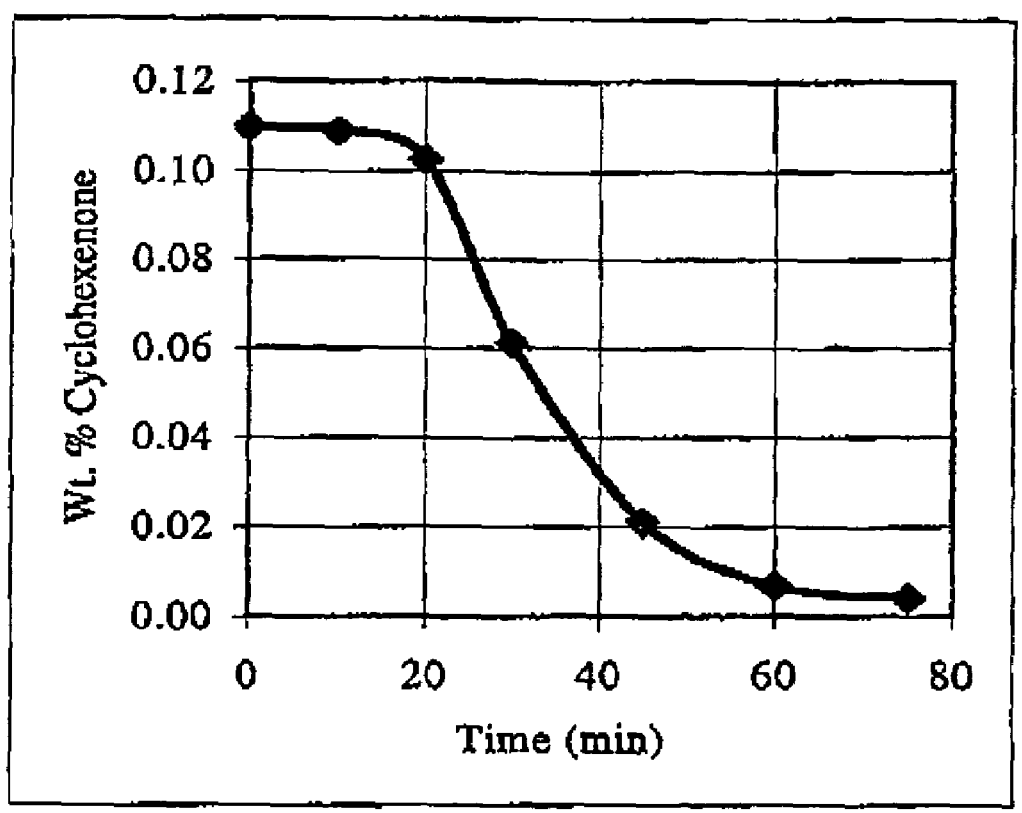
FIG. 2 is a graphical representation of the amount of cyclohexenone in an organic mixture as a function of time in the presence of an alkali hydroxide.

Using the same experimental set-up as described in Example 1, a 200 mL mixture representing a cyclohexane oxidation mixture containing 65.19 wt % cyclohexane, 21.54 wt % cyclohexanone, 13.17 wt % cyclohexanol and 0.11 wt % 2-cyclohexene-1-one was charged to the reactor. 3 g of 25 wt % NaOH solution was also added. The mixture was heated to and maintained at 85 degrees C. for approximately 75 minutes while continuously stirring. The addition of the NaOH resulted in a decreased concentration of cyclohexenone in the mixture over time, the results of which are shown in FIG. 2. These results demonstrate that the cyclohexenone concentration in an organic mixture, such as an organic mixture that results from the oxidation of cyclohexane, may be reduced by approximately 96% using methods according to exemplary embodiments of the invention.

The present invention is not to be limited in scope by the specific embodiments described herein. Indeed, various modifications of the present invention, in addition to those described herein, will be apparent to those of ordinary skill in the art from the foregoing description. Thus, such modifications are intended to fall within the scope of the following appended claims. Further, although the present invention has been described herein in the context of a particular implementation in a particular environment for a particular purpose, those of ordinary skill in the art will recognize that its usefulness is not limited thereto and that the present invention can be beneficially implemented in any number of environments for any number of purposes. Accordingly, the claims set forth below should be construed in view of the full breadth and spirit of the present invention as disclosed herein.

What is claimed is:

1. A method for reducing a concentration of cyclohexenone in an organic mixture comprising cyclohexenone, the method comprising treating the organic mixture with an effective amount of additive comprising at least one of sulfurous acid, a salt of sulfurous acid, or an alkali hydroxide.

2. The method of claim 1 wherein the organic mixture is treated at a temperature in the range of about 60 to about 160 degrees C.

3. The method of claim 1 wherein the organic mixture is treated for about 10 to about 90 minutes.

4. The method of claim 1 wherein the organic mixture is created with at least one of sulfurous acid, sodium hydrogen sulfite, sodium metabisulfite, sodium sulfite or a mixture of two or more of these compounds.

5. The method of claim 1 wherein the organic mixture is treated with a salt of sulfurous acid and wherein the organic mixture is further treated with sodium carbonate.

6. The method of claim 1 wherein the organic mixture is treated with sodium hydrogen sulfite.

7. The method of claim 1 wherein the organic mixture is treated with sodium hydrogen sulfite and sodium carbonate.

8. The method of claim 1 wherein the organic mixture is treated with sodium hydroxide, potassium hydroxide, or a mixture of the two.

9. The method of claim 8 wherein the organic mixture is treated with sodium hydroxide.

10. The method of claim 8 comprising adding cyclohexanone to the organic mixture.

11. The method of claim 1 wherein the organic mixture comprises cyclohexanone and cyclohexenone.

12. The method of claim 11 wherein the organic mixture further comprises cyclohexanol.

13. The method of claim 1 wherein the organic mixture is obtained by a process of oxidizing cyclohexane.

14. The method of claim 1 wherein the organic mixture comprises cyclohexanol and cyclohexenone.

15. The method of claim 14 wherein the organic mixture is treated with sulfurous acid, sodium hydrogen sulfite, sodium metabisulfite, sodium sulfite or a mixture of two or more of these compounds.

16. The method of claim 15 wherein the organic mixture is also treated with sodium carbonate.

17. The method of claim 1 wherein the organic mixture is obtained by a process of dehydrogenating a mixture comprising cyclohexenone and cyclohexanol.

18. The method of claim 1 wherein the organic mixture comprises cyclohexanol and cyclohexanone and the mixture is treated following a dehydrogenation process.

19. The method of claim 1 wherein the additive is added in amount effective to reduce the concentration of cyclohexenone by about 75%.

20. The method of claim 1 wherein the additive is added in amount effective to reduce the concentration of cyclohexenone by about 90%.

21. The method of claim 1 wherein the cyclohexenone is 2-cyclohexene-1-one.

22. The method of claim 1 wherein the organic mixture comprises cyclohexanol obtained by a process of producing cyclohexanol from phenol.

23. A method of reducing a concentration of 2-cyclohexene-1-one in an organic mixture comprising cyclohexenone and cyclohexanone, the method comprising treating the organic mixture with an effective amount of an additive selected from the group consisting of sulfurous acid, a salt of sulfurous add, an alkali hydroxide, or a mixture of two or more of these compounds.

* * * * *